United States Patent
Zwickl

(10) Patent No.: US 10,918,612 B2
(45) Date of Patent: Feb. 16, 2021

(54) COMBINATIONS WITH 2-AMINOETHANESULFONIC ACID

(71) Applicant: Markus Zwickl, Mittelbiberach (DE)

(72) Inventor: Markus Zwickl, Mittelbiberach (DE)

(73) Assignee: Markus Zwickl, Mittelbiberach (DE)

( * ) Notice: Subject to any disclaimer, the term of this patent is extended or adjusted under 35 U.S.C. 154(b) by 371 days.

(21) Appl. No.: 14/157,986

(22) Filed: Jan. 17, 2014

(65) Prior Publication Data
US 2014/0206674 A1    Jul. 24, 2014

(30) Foreign Application Priority Data

Jan. 22, 2013  (EP) .................................... 13152170
Apr. 16, 2013  (EP) .................................... 13163915

(51) Int. Cl.
| | |
|---|---|
| *A61K 31/00* | (2006.01) |
| *A61K 45/00* | (2006.01) |
| *A61K 31/185* | (2006.01) |
| *A61K 31/216* | (2006.01) |
| *A61K 31/4184* | (2006.01) |
| *A61K 31/4422* | (2006.01) |
| *A61K 31/549* | (2006.01) |
| *A61K 31/5513* | (2006.01) |
| *A61K 31/4035* | (2006.01) |
| *A61K 45/06* | (2006.01) |
| *A61K 31/4178* | (2006.01) |
| *A61K 31/41* | (2006.01) |
| *A61K 31/4245* | (2006.01) |

(52) U.S. Cl.
CPC .......... *A61K 31/185* (2013.01); *A61K 31/216* (2013.01); *A61K 31/4035* (2013.01); *A61K 31/41* (2013.01); *A61K 31/4178* (2013.01); *A61K 31/4184* (2013.01); *A61K 31/4245* (2013.01); *A61K 31/4422* (2013.01); *A61K 31/549* (2013.01); *A61K 31/5513* (2013.01); *A61K 45/06* (2013.01)

(58) Field of Classification Search
CPC .. A61K 31/195; A61K 31/41; A61K 31/4178; A61K 31/4184; A61K 45/06
See application file for complete search history.

(56) References Cited

U.S. PATENT DOCUMENTS

| | | | | |
|---|---|---|---|---|
| 4,545,977 A | * | 10/1985 | Gaull | 514/559 |
| 4,826,679 A | * | 5/1989 | Roy | 424/94.21 |
| 4,842,846 A | * | 6/1989 | Nakano | 424/50 |
| 6,015,835 A | | 1/2000 | Miyamoto et al. | |
| 6,099,869 A | * | 8/2000 | McCarty | 424/696 |
| 2004/0161407 A1 | * | 8/2004 | Kimura | A61K 9/02 424/85.7 |
| 2005/0222137 A1 | * | 10/2005 | Shetty et al. | 514/223.5 |

FOREIGN PATENT DOCUMENTS

| | | | |
|---|---|---|---|
| CN | 102600140 A | * | 7/2012 |
| WO | WO 2010089355 A1 | * | 8/2010 |

OTHER PUBLICATIONS

Tsuboyama-Kasaoka et al., "Taurine (2-Aminoethanesulfonic Acid) Deficiency Creates a Vicious Circle Promoting Obesity", Endocrinology, 2006, vol. 147, No. 7, pp. 3276-3284.*
English machine translation of CN 102600140 A, accessed from Google, May 26, 2015.*
Chemical Abstracts Service Registry No. 111470-99-6, Norvasc (amlodipine). Accessed from SciFinder on Dec. 27, 2016.*
Chemical Abstracts Service Registry No. 145040-37-5, Blopress (candesartan). Accessed from SciFinder on Dec. 27, 2016.*
Oparil, Am. J. Hypertension, 2000, vol. 13, No. 1 part 2, pp. 18S-24S (Year: 2000).*
International Search Report for PCT/EP2014/051098 dated May 12, 2014.
Kimura, Akihiko et al. "Large Amounts of 1b-Hydroxylated Bile Acids in Urine during Taurine Therapy" The Kurume Medical Journal (1992) vol. 39, pp. 105-111.
Lidsky, T.I. et al. "Taurine prevents haloperidol-induced changes in striatal neurochemistry and behavior" Brain Research 686 (1995) pp. 104-106.
Imayama et al., "Telmisartan downregulates angiotensin II type 1 receptor through activation of peroxisome proliferator-activated receptor", Cardiovascular Research, 2006, 72, pp. 184-190.
Ahmadian et al., "Taurine supplementation has antiatherogenic and anti-nflammatory effects before and after incremental exercise in heart failure", Therapeutic Advances in Cardiovascular Disease, 2017, vol. 11(7), pp. 185-194.

* cited by examiner

*Primary Examiner* — Sikarl A Witherspoon
(74) *Attorney, Agent, or Firm* — Hoxie & Associates LLC

(57) ABSTRACT

The invention relates to a pharmaceutical combination of 2-aminoethanesulfonic acid with a pharmaceutical agent such as an antihypertensive agent and the use of 2-aminoethanesulfonic acid in a method to lower the bilirubin level in the blood.

7 Claims, No Drawings

COMBINATIONS WITH 2-AMINOETHANESULFONIC ACID

The present invention relates to the use of 2-aminoethanesulfonic acid in combination with a therapeutically active agent such as an antihypertensive agent.

2-aminoethanesulfonic acid (also known as tauric acid or taurine) is an unusual biological non-protein β-amino acid with a sulfonic acid group in place of the carboxyl group:

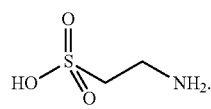

Though found in most tissues the endogenous production of 2-aminoethanesulfonic acid is insufficient in humans and needs to be supplemented with food such as fish and meat. It crosses the blood-brain barrier and is described to have antioxidative properties, to regulate intracellular $Ca^{2+}$, to be involved in osmoregulation as an osmolyte, and to modulate inflammatory reactions and neuronal activity. In cats 2-aminoethanesulfonic acid appears to be a trophic factor in the retina. In some pathological conditions including diabetes lowered tissue concentrations of 2-aminoethanesulfonic acid are found, and it has been reported that supplementation with 2-aminoethanesulfonic acid has the potential to attenuate said conditions.

With increasing age a large proportion of the adult population develops elevated blood pressure also referred to as "essential hypertension", i.e. systolic blood pressure (SBP) higher than 120 mm Hg and diastolic blood pressure higher than 80 mm Hg. The hypertension leads to ventricular hypertrophy and is often combined with hyperlipidaemia. Both symptoms are serious risk factors for cardiovascular diseases leading to cardiovascular events such as myocardial infarction or stroke. Elevated blood cholesterol and lipid levels are involved in atherosclerosis, a condition characterized by unevenly distributed lipid deposits inside the arteries.

Different modes of anti-hypertensive action are known and a variety of different anti-hypertensive drugs are available. Examples of such antihypertensive drugs are diuretics, calcium channel blockers (CCBs) and angiotensin receptor blockers (ARBs). Preferred embodiments of said examples are

- the diuretics hydrochlorothiazide and chlorthalidone,
- the CCBs amlodipine and nifedipine,
- the ARBs candesartan, irbesartan, losartan, olmesartan, telmisartan, valsartan, and
- pharmaceutically acceptable salts thereof.

Diuretics reduce blood pressure by causing the kidneys to increase the amount of salt and water eliminated with the urine.

CCBs reduce blood pressure by interfering with the movement of $Ca^{2+}$ ions through voltage-gated calcium channels resulting in a decrease of intracellular calcium.

ARBs reduce blood pressure by blocking receptor sites of the peptide hormone angiotensin II resulting in vasoconstriction and increased blood pressure.

According to the present invention the bilirubin level in the blood of individuals with increased bilirubin levels (about 10% of the population) is decreased or lowered by supplementing their alimentation with 2-aminoethanesulfonic acid. In view of this surprising and unexpected finding individuals with an increased bilirubin level also benefit from treatment with a pharmaceutical preparation comprising 2-aminoethanesulfonic acid either alone or comprising an additional therapeutically active agent. Such a pharmaceutical preparation is particularly beneficial for an individual having one or two UGT1A1*28 alleles such as an individual suffering from the Gilbert syndrome.

Additionally an unexpected increase of the thyroid stimulating hormone TSH (measured as tsh-basal) is observed. Such a TSH increase is known to result in stimulation of the thyroid gland to produce the thyroid hormones, which in turn increases the basal metabolic rate. In view of this surprising and unexpected finding, individuals suffering from a thyroid hormone imbalance benefit from 2-aminoethanesulfonic acid supplementation, which stabilizes their metabolic rate.

To reliably implement an individual's 2-aminoethanesulfonic acid intake it is desirable to combine the 2-aminoethanesulfonic acid with a therapeutic agent which the individual already takes daily. Examples of such therapeutic agents are antihypertensives, antidiabetics and lipid lowering agents. Particularly preferred are antihypertensives.

Antihypertensive treatment, i.e. reduction of elevated blood pressure, has been shown to result in various clinical benefits such as reductions in cardiovascular mortality and morbidity, stroke, and the incidence of dementia. However, in a high proportion of patients treatment with a single active agent does not suffice to reach the target blood pressures of SBP below 140 mm Hg and DBP below 90 mm Hg, which in the case of patients additionally diagnosed for diabetes should even be SBP below 130 mm Hg and DBP below 80 mm Hg. Therefore, said patients need to be treated with a combination of two or three different antihypertensive agents to reach their beneficial target blood pressures.

Though 2-aminoethanesulfonic acid alone is reported to exert an antihypertensive effect it has not been recognized that the antihypertensive effect of treatment with a diuretic, calcium channel blocker or angiotensin receptor blocker can be further increased by combining said treatment with a 2-aminoethanesulfonic acid treatment. The present invention for the first time teaches, that daily blood pressure treatment with a diuretic, a CCB or an ARB combined with a 2-aminoethanesulfonic acid treatment can result in an additional or synergistic blood pressure reduction as compared to treatment with the antihypertensive diuretic, CCB or ARB alone. Simultaneously the homeostatic properties associated with 2-aminoethanesulfonic acid stabilize the reduced blood pressure over the 24 hour treatment period and reduce the incidence of a number of adverse events such as hypotension, syncope or arrhythmia. While 2-aminoethanesulfonic acid can be administered separately, administration of the antihypertensive and 2-aminoethanesulfonic acid in a single dosage form improves patient compliance and, thus, insures that a blood pressure patient takes advantage of the additional benefits associated with 2-aminoethanesulfonic acid treatment. 2-aminoethanesulfonic acid represents an endogenously produced component of blood pressure regulation and is not a customary antihypertensive agent. Therefore, using a therapeutic combination of an antihypertensive agent with 2-aminoethanesulfonic acid has the additional advantage, that no or less additional antihypertensive agent is needed to achieve the beneficial target blood pressure. Additionally, the effect on the thyroid hormones stabilizes the patient's metabolic rate. In individuals with increased bilirubin levels said level is unexpectedly decreased. Thus, hypertensive individuals with an increased bilirubin level additionally benefit from treatment with 2-aminoethanesulfonic acid.

Further benefits of combining a diuretic, CCB or ARB with 2-aminoethanesulfonic acid are
- increased generation of the vasodilator NO;
- increase of intracellular $Ca^{2+}$ concentrations to maintain calcium homeostasis;
- decreased LOX-1 expression;
- decreased serum concentration of C-reactive protein (CRP);
- membrane stabilization and mitigated development of arterial stiffness, improved vascular relaxation, endothelial apoptosis, oxidative stress and inflammation particularly in diabetic patients;
- improved lipid metabolism particularly in overweight individuals resulting in reduced serum cholesterol, reduced triglyceride or even reduced body weight;
- improved sleep;
- decreased atherogenic index;
- reduced blood platelet aggregation;
- prevention of the formation of advanced glycation end products (AGE);
- protective effects against renal damage, cataracts and glaucoma; and
- neuroprotection for example with respect to Alzheimer's disease.

Beneficial effects are not only observed in the treatment of hypertension but also in the treatment of conditions such as congestive heart failure, hypercholesterolemia, retinal disorders, neurodegenerative diseases such as Alzheimer's, Parkinson's or Huntington's disease and hepatic problems such as the Gilbert Syndrome.

Thus, 2-aminoethanesulfonic acid cooperates favourably with an antihypertensive diuretic, calcium channel blocker or ARB, for example, in the treatment or prevention of congestive heart failure, cardiovascular disease, stroke, transient ischemic attack, myocardial infarction, dyslipidemia, cognitive decline or dementia.

About 10% of the population are affected by the Gilbert Syndrome, i.e. a mutation in the UGT1A1 gene (UGT1A1*28). This means that about 10% of the hypertensive patients also have reduced bilirubin conjugation and unconjugated hyperbilirubinemia. In these patients 2-aminoethanesulfonic acid accelerates biliary excretion of bilirubin providing neuroprotection against bilirubin-induced elevation of apoptosis and intracellular free $Ca^{2+}$. Additionally, the added 2-aminoethanesulfonic acid supports the prevention of gallstone formation. Despite the increased excretion of bilirubin, which has favourable antioxidative properties, the antioxidative potential is maintained by the antioxidative properties of 2-aminoethanesulfonic acid. Thus, the present invention for the first time recognizes that low cancer mortality, found associated with elevated bilirubin levels, should be advantageously maintained by supplemented 2-aminoethanesulfonic acid.

Object of the present invention is to provide an oral pharmaceutical preparation comprising 2-aminoethanesulfonic acid and an antihypertensive agent selected from the group consisting of a diuretic, a calcium channel blocker (CCB), or an angiotensin receptor blocker (ARB) including a pharmaceutically acceptable salt thereof. Optimized combinations consist of the two ingredients in admixture with one or more excipients (adjuvants). Particularly preferred preparations are capsule, tablet or effervescent tablet dosage forms. Tablets may comprise a single, two or more layers.

2-aminoethanesulfonic acid also favourably cooperates with a therapeutically active (in particular antipsychotic, antidepressant, antiplatelet, antidiabetic or antihyperlipidemic) agent such as olanzapine (about 2.5-20 mg), pramipexole (0.1-1 mg), ropinirol (0.5-4 mg), duloxetine (about 20-60 mg), escitalopram (about 4-8 mg), risperidone (about 0.25-4 mg), clopidogrel (about 75 mg), sitagliptin (about 25-100 mg), fenofibrate (about 40-120 mg) or benzafibrat (about 200 mg). Preferably, 2-aminoethanesulfonic acid is combined with an active agent, the metabolism of which does not rely on the UGT1A1 encoded gene product.

Examples of suitable excipients (adjuvants) are mannitol, sorbitol, xylit, saccharose, calciumcarbonat, calciumphosphat, lactose, croscarmellose sodium salt (cellulose carboxymethylether sodium salt, cross linked), crospovidone, sodium starch glycolate, hydroxypropylcellulose (low substituted), maize starch, polyvinylpyrrolidon, copolymers of vinylpyrrolidon with other vinylderivatives (copovidones), hydroxypropyl cellulose, hydroxypropylmethyl cellulose, microcristalline cellulose or starch, magnesiumstearat, sodiumstearylfumarat, talc, hydroxypropylmethylcellulose, carboxymethylcellulose, celluloseacetatphthalat, polyvinylacetat, water, water/ethanol, water/glycerine, water/sorbit, water/polyethylenglykol, propylenglykol, cetylstearylalkohol, carboxymethylcellulose or substances containing fat such as hard grease.

Various excipients are usually included for different purposes:
- Mannitol, sorbitol, xylit, saccharose, calciumcarbonat, calciumphosphat and lactose are examples of inert diluents;
- croscarmellose sodium salt (cellulose carboxymethylether sodium salt, cross linked), crospovidone, sodium starch glycolate, hydroxypropylcellulose (low substituted) and maize starch are examples of disintegrants, sodium starch glycolate being preferred;
- polyvinylpyrrolidon, copolymers of vinylpyrrolidon with other vinylderivatives (copovidones), hydroxypropyl cellulose, hydroxypropylmethyl cellulose, microcristalline cellulose or starch are binders;
- magnesiumstearat, sodiumstearylfumarat and talc have the function of lubricants;
- examples for agents delaying release are hydroxypropylmethyl cellulose, carboxymethyl cellulose, celluloseacetatphthalat and polyvinyl acetate; and
- ferric oxides are dyes acceptable for pharmaceutically use.

Preferred embodiments of the present invention are pharmaceutical preparations, wherein the antihypertensive agent is selected from the group consisting of hydrochlorothiazide, chlorthalidone, amlodipine, nifedipine, telmisartan, irbesartan, valsartan, candesartan, losartan, olmesartan, azilsartan or a pharmaceutically acceptable salt thereof.

Examples of preferred pharmaceutical preparations comprise chlorthalidone, hydrochlorothiazide or amlodipine or a pharmaceutically acceptable salt thereof such as amlodipine besylate.

Particularly preferred is a pharmaceutical preparation, wherein the angiotensin receptor blocker is telmisartan or the sodium or calcium salt thereof.

In a preferred embodiment the capsule or tablet comprises 2-aminoethanesulfonic acid and telmisartan or a pharmaceutically acceptable salt thereof together with the excipients sorbitol and magnesium stearate, compressed directly into tablets.

In a particularly preferred embodiment the excipient is selected from the group consisting of mannitol, sorbitol, xylit, saccharose, calciumcarbonat, calciumphosphat, lactose, croscarmellose sodium salt (cellulose carboxymethylether sodium salt, cross linked), crospovidone, sodium starch glycolate, Hydroxypropylcellulose (low substituted), maize starch, polyvinylpyrrolidon, copolymers of vinylpyrrolidon with other vinylderivatives (copovidones), hydroxypropyl cellulose, hydroxypropylmethyl cellulose, microcristalline cellulose or starch, magnesiumstearat, sodiumstearylfumarat, talc, hydroxypropylmethylcellulose, carboxymethylcellulose, celluloseacetatphthalat, polyvinylacetat, water, water/ethanol, water/glycerine, water/sorbit, water/polyethylenglykol, propylenglykol, cetylstearylalkohol, carboxymethylcellulose or substances containing fat.

The amount of diuretic in a single dosage form is usually in the range of 10-50 mg of the diuretic such as HCTZ or chlorthalidone.

The amount of CCB in a single dosage form is usually in the range of a 1-100 mg of CCB such as 5-10 mg of amlodipine or 10-90 mg of nifedipine.

The amount of ARB in a single dosage form is usually in the range of 10-800 mg, depending on the ARB used. Preferred ranges are 150-300 mg (e.g. irbesartan), 60-90 mg (e.g. valsartan or telmisartan), 20-90 mg (e.g. telmisartan or losartan) or 15-30 mg (e.g. candesartan). Particularly preferred are 80-85 mg, 40-45 mg or 20-25 mg.

The amount of 2-aminoethanesulfonic acid in a single dosage form is usually in the range of 250-1000 mg and the weight ratio of 2-aminoethanesulfonic acid to, for example, telmisartan or a polymorph or salt thereof is in the range of 25:1 to 5:1.

Thus, tablets according to the present invention can contain 20-200 mg, preferably 60-90 mg or 30-60 mg telmisartan or its sodium salt, and 300-600 mg, 2-aminoethanesulfonic acid.

Particularly preferred are amounts of 80-85 mg or 40-45 mg telmisartan or its sodium salt and 250 mg or 500 mg 2-aminoethanesulfonic acid.

In said tablets 2-aminoethanesulfonic acid can be additionally combined with a diuretic such as 10-50 mg HCTZ or chlorthalidone, or a CCB such as 5-10 mg amlodipine.

Another embodiment of the present invention is a method of producing an oral capsule or tablet or effervescent tablet dosage form comprising mixing 2-aminoethanesulfonic acid and an antihypertensive agent selected from the group consisting of a diuretic, a calcium channel blocker, and an angiotensin receptor blocker with one or more pharmaceutically acceptable excipients.

The specific preparations according to the present invention are used to treat hypertension in a mammal while implicating a number of unexpected therapeutic benefits such as increased generation of NO and intracellular $Ca^{2+}$ concentrations;
improved lipid metabolism and sleep; and
mitigated arterial stiffness;
protective effects against renal damage, retinal disorders, cataract, glaucoma; congestive heart failure, hypercholesterolemia, hepatic problems and Alzheimer's disease.

Therefore, the preparations according to the invention can be used to additionally treat or prevent cardiovascular events, left ventricular hypertrophy, stroke, cardiac insufficiency (heart failure), myocardial infarction, diabetic nephropathy or diabetic retinopathy. In particular they additionally reduce the risk of transient ischemic attacks, stroke, myocardial infarction, progression of cardiac insufficiency after cardiovascular events selected from the group consisting of myocardial infarction, left ventricular hypertrophy, diabetic nephropathy or retinopathy, and any kind of cardiovascular death.

In a preferred embodiment preparations of the present invention are used to treat human patients in whom the prevention or treatment of cardiovascular, cardiopulmonary or renal diseases is indicated or carrying the UGT1A1*28 mutation, with a preparation comprising a diuretic, CCB or an ARB such as telmisartan in combination with 2-aminoethanesulfonic acid optionally with one or more excipients.

By combining an antihypertensive agent such as a diuretic, a CCB or and ARB with 2-aminoethanesulfonic acid an additional reduction in systolic and diastolic blood pressure is achieved. This is even more beneficial taking into account the additional therapeutic and preventive benefits due to the combination with 2-aminoethanesulfonic acid such as increased generation of NO and intracellular $Ca^{2+}$ concentrations;
improved lipid metabolism with decreased atherogenic index; and
mitigated development of arterial stiffness, oxidative stress and inflammation.

To produce a pharmaceutical preparation for oral administration according to the invention procedures known in the art can be used. Suitable excipients for the compression of diuretics, CCBs or ARBs with 2-aminoethanesulfonic acid after mixing are sorbitol and magnesiumstearat, which can be replaced by other excipients such as mannitol or saccharose. Occasionally the properties of tablets can be modified by granulation of the antihypertensive agent or 2-aminoethanesulfonic acid or both with selected excipients before final compression of all the components of the pharmaceutical preparation. For this purpose the diuretic, CCB, ARB or salt thereof is mixed, for example, with mannitol, hydroxypropyl cellulose and, optionally, a colouring agent in a suitable blender. The resulting blend is preferably sieved and can be subjected to a dry granulation process in a roller compactor. The mentioned excipients might be replaced by other adjuvants such as lactose or microcristalline cellulose. The resulting granulate can be mixed with 2-aminoethanesulfonic acid and other excipients such as mannitol, microcristalline cellulose, sodium starch glycolate, magnesium stearate and optionally a colouring agent before being compressed to tablets. Alternatively, adjuvants such as lactose or croscarmellose sodium salt can be used.

It is preferred that the dosage form comprising a diuretic, CCB or ARB and 2-aminoethanesulfonic acid has fast dissolution and immediate drug release properties combined with adequate stability. In case mere combination of the active ingredients is not practical due to incompatibilities with excipients used in the mono-dosage form of the active ingredients, it is possible to coat 2-aminoethanesulfonic acid particles in a fluidized-bed granulator with a polymer solution containing water soluble polymers like hydroxypropylcellulose, hydroxypropylmethylcellulose or polyvinylpyrrolidone, thereby reducing the contact surface area of the 2-aminoethanesulfonic acid particles with the other components of the dosage form.

The dissolving tablet matrix may have acidic, neutral or basic properties. For the ARB telmisartan for example a basic tablet matrix is preferred. In this embodiment, the dissolving matrix comprises a basic agent, a water-soluble diluent and, optionally, other excipients (adjuvants). Specific examples of suitable basic agents are alkali metal hydroxides such as NaOH and KOH; basic amino acids such as arginine and lysine; and meglumine (N-methyl-D-glucamine), NaOH and meglumine being preferred.

Other (optional) constituents may, for instance, be chosen from one or more of the following excipients and/or adjuvants in the amounts indicated:

10 to 30 wt. %, preferably 15 to 25 wt. %, of binders, carriers and fillers, thereby replacing the water-soluble diluents;
0.1 to 5 wt. %, preferably 0.5 to 3 wt. %, of lubricants;
0.1 to 5 wt. %, preferably 0.3 to 2 wt. %, of flow control agents;
1 to 10 wt. %, preferably 2 to 8 wt. %, of crystallization retarders;
1 to 10 wt. %, preferably 2 to 8 wt. %, of solubilizers;
0.05 To 1.5 wt. %, preferably 0.1 to 0.8 wt. %, of colouring agents;
0.5 to 10 wt. %, preferably 2 to 8 wt. %, of pH control agents;
0.01 to 5 wt. %, preferably 0.05 to 1 wt. %, of surfactants and emulsifiers.

The tablets prepared release the diuretic, CCB or ARB and 2-aminoethanesulfonic acid rapidly and in a largely pH-independent fashion, with complete release occurring within less than 90 min and release of the major fraction occurring within less than 30 min.

The following examples illustrate the subject matter of the invention.

EXAMPLE 1

40 mg Telmisartan and 250 mg 2-aminoethane-sulfonic Acid Tablet

| Constituents | mg per tablet | % per tablet |
|---|---|---|
| Telmisartan | 40.000 | 8.421 |
| Taurine | 250.000 | 52.632 |
| Sodium hydroxide | 3.360 | 0.707 |
| Meglumine | 12.000 | 2.526 |
| Povidone | 12.000 | 2.526 |
| Sorbitol | 150.640 | 31.714 |
| Magnesium stearate | 7.000 | 1.474 |
| Total Telmisartan layer | 475.000 | 100.000 |

EXAMPLE 2

40 mg Telmisartan and 500 mg 2-aminoethanesulfonic Acid Tablet

| Constituents | mg per tablet | % per tablet |
|---|---|---|
| Telmisartan | 40.000 | 5.714 |
| Taurine | 500.000 | 71.429 |
| Sodium hydroxide | 3.360 | 0.480 |
| Meglumine | 12.000 | 1.714 |
| Povidone | 12.000 | 1.714 |
| Sorbitol | 125.640 | 17.949 |
| Magnesium stearate | 7.000 | 1.000 |
| Total Telmisartan layer | 700.000 | 100.000 |

EXAMPLE 3

40 mg Telmisartan and 500 mg 2-aminoethanesulfonic Acid Capsule

| Constituents | mg per capsule | % per capsule |
|---|---|---|
| Telmisartan | 40.000 | 5.714 |
| Taurine | 500.000 | 71.429 |
| Meglumine | 40.000 | 5.714 |
| Crystalline cellulose | 20.000 | 2.857 |
| Poloxamer 188 | 8.000 | 1.143 |
| Povidone | 12.000 | 1.714 |
| D-mannitol | 79.000 | 11.286 |
| Magnesium stearate | 1.000 | 0.143 |
| Total Telmisartan layer | 700.000 | 100.000 |

EXAMPLE 4

5 mg Amlodipine and 250 mg 2-aminoethane-sulfonic Acid Tablet

| Constituents | mg per tablet | % per tablet |
|---|---|---|
| Amlodipine besylate | 6.944 | 1.543 |
| Taurine | 250.000 | 55.556 |
| Microcrystalline cellulose | 100.000 | 22.222 |
| Dibasic calcium phosphate | 85.556 | 19.012 |
| Sodium starch glycolate | 6.000 | 1.333 |
| Magnesium stearate | 1.500 | 0.333 |
| Total Telmisartan layer | 450.000 | 100.000 |

EXAMPLE 5

5 mg Amlodipine and 500 mg 2-aminoethanesulfonic Acid Tablet

| Constituents | mg per tablet | % per tablet |
|---|---|---|
| Amlodipine besylate | 6.944 | 0.992 |
| Taurine | 500.000 | 71.729 |
| Microcrystalline cellulose | 100.000 | 14.286 |
| Dibasic calcium phosphate | 85.556 | 12.222 |
| Sodium starch glycolate | 6.000 | 0.857 |
| Magnesium stearate | 1.500 | 0.214 |
| Total Telmisartan layer | 700.000 | 100.000 |

EXAMPLE 6

10 mg Amlodipine and 500 mg 2-aminoethanesulfonic Acid Capsule

| Constituents | mg per capsule | % per capsule |
|---|---|---|
| Amlodipine besylate | 12.840 | 1.427 |
| Taurine | 500.000 | 55.556 |
| Microcrystalline cellulose | 200.000 | 22.222 |
| Pregelatinized starch | 171.160 | 19.018 |
| Sodium starch glycolate | 12.000 | 1.333 |
| Colloidal silicon dioxide | 2.000 | 0.222 |
| Magnesium stearate | 2.000 | 0.222 |
| Total Telmisartan layer | 900.000 | 100.000 |

EXAMPLE 7

12.5 mg HCTZ and 250 mg 2-aminoethane-sulfonic Acid Tablet

| Constituents | mg per tablet | % per tablet |
|---|---|---|
| Taurine | 250.000 | 55.556 |
| Hydrochlorothiazide (HCTZ) | 12.500 | 2.778 |
| Lactose monohydrate | 112.500 | 25.000 |
| Microcrystalline cellulose | 64.000 | 14.222 |
| Corn starch | 6.000 | 1.333 |
| Sodium starch glycolate | 4.000 | 0.889 |
| Magnesium stearate | 1.000 | 0.222 |
| Total Telmisartan layer | 450.000 | 100.000 |

EXAMPLE 8

25.0 mg HCTZ and 250 mg 2-aminoethane-sulfonic Acid Tablet

| Constituents | mg per tablet | % per tablet |
|---|---|---|
| Taurine | 250.000 | 55.556 |
| Hydrochlorothiazide (HCTZ) | 25.000 | 2.778 |
| Lactose monohydrate | 100.000 | 25.000 |
| Microcrystalline cellulose | 64.000 | 14.222 |
| Corn starch | 6.000 | 1.333 |
| Sodium starch glycolate | 4.000 | 0.889 |
| Magnesium stearate | 1.000 | 0.222 |
| Total Telmisartan layer | 450.000 | 100.000 |

EXAMPLE 9

12.5 mg HCTZ and 500 mg 2-aminoethane-sulfonic Acid Tablet

| Constituents | mg per tablet | % per tablet |
|---|---|---|
| Hydrochlorothiazide (HCTZ) | 12.500 | 2.778 |
| Taurine | 250.000 | 55.556 |
| Lactose monohydrate | 112.500 | 25.000 |
| Microcrystalline cellulose | 64.000 | 14.222 |
| Corn starch | 6.000 | 1.333 |
| Sodium starch glycolate | 4.000 | 0.889 |
| Magnesium stearate | 1.000 | 0.222 |
| Total Telmisartan layer | 700.000 | 100.000 |

EXAMPLE 10

20 mg Telmisartan and 250 mg 2-aminoethane-sulfonic Acid Tablet

| Constituents | mg per tablet | % per tablet |
|---|---|---|
| Telmisartan | 20.000 | 4.444 |
| Taurine | 250.000 | 55.556 |
| Sodium hydroxide | 1.680 | 0.373 |
| Meglumine | 12.000 | 2.667 |
| Povidone | 12.000 | 2.667 |
| Sorbitol | 147.320 | 32.738 |
| Magnesium stearate | 7.000 | 1.556 |
| Total Telmisartan layer | 450.000 | 100.000 |

EXAMPLE 11

20 mg Telmisartan, 5 mg Amlodipine, 12.5 mg HCTZ and 250 mg 2-aminoethane-sulfonic Acid Tablet

| Constituents | mg per tablet | % per tablet |
|---|---|---|
| Telmisartan | 20.000 | 4.000 |
| Amlodipine besylate | 6.944 | 1.389 |
| Hydrochlorothiazide (HCTZ) | 12.500 | 2.500 |
| Taurine | 250.000 | 52.632 |
| Sodium hydroxide | 1.680 | 0.336 |
| Meglumine | 12.000 | 2.400 |
| Povidone | 12.000 | 2.400 |
| Sorbitol | 177.876 | 35.575 |
| Magnesium stearate | 7.000 | 1.400 |
| Total Telmisartan layer | 500.000 | 100.000 |

EXAMPLE 12

Effect of Treatment with 2-aminomethanesulfonic Acid

The last three columns of Table 1 show hemogram parameters compiled on different dates for an individual later diagnosed to carry in the promoter region of both UGT1A1 alleles 7 TA-repeats instead of 6 TA-repeats corresponding to the genotype UGT1A1*28/*28. This is in line with the increased values for total bilirubin, which should normally be in the range of 0.2 to 1.2 mg/dl. The individual did not receive any treatment.

TABLE 1

| Parameter | Unit | analysis 1 of March 2006 | analysis 2 of January 2009 | analysis 3 of March 2011 |
|---|---|---|---|---|
| Total Bilirubin | mg/dl | 2.4 | 2.3 | |
| creatinin | mg/dl | 1.1 | 0.9 | 0.89 |
| Uric acid | mg/dl | 5.1 | 4.1 | 4.7 |
| triglyceride | mg/dl | 65 | 70 | 56 |
| Total cholesterol | mg/dl | 176 | 177 | 174 |
| HDL-cholesterol | mg/dl | 68 | 61 | 80 |
| LDL-cholesterol | mg/dl | 107 | 97 | 82 |
| glucose | mg/dl | 84 | 93 | 87 |
| ferritin | µg/l | | 179 | 197 |
| erythrocytes | Mio/µl | 5 | 5.1 | 4.8 |
| haemoglobin | g/dl | 14.1 | 14.5 | 14.3 |
| hematocrit | l/l | 0.42 | 0.4 | 0.42 |
| MCV | fL | 85 | 78.3 | 88.7 |
| MCH | pg | 28 | 28 | 30 |
| MCHC | g/dl | 33 | 36 | 34 |
| thrombocytes | /nl | 193 | 229 | 193 |
| tsh basal | µU/ml | 1.19 | 1.2 | 1.38 |

The third column of Table 2 shows the average values of the three hemograms of Table 1 while the fourth column shows the parameters compiled on a day after the individual has been daily treated for at least 3 months with 400 to 500 mg of 2-aminomethanesulfonic acid. The fifth column calculates the difference of the values in the forth and third column in % of the value in the third column. Thus, the fifth column describes the change of the value in the third column caused by the individual's treatment with 2-aminomethanesulfonic acid.

TABLE 2

| Parameter | Unit | average of analysis 1 to 3 | analysis of March 2013 | Difference/% |
|---|---|---|---|---|
| total Bilirubin | mg/dl | 2.4 | 1.35 | −43 |
| creatinin | mg/dl | 1.0 | 0.94 | −6 |
| Uric acid | mg/dl | 4.6 | 4.01 | −13 |
| triglyceride | mg/dl | 63.7 | 39 | −39 |
| total cholesterol | mg/dl | 175.7 | 188 | 7 |
| HDL-cholesterol | mg/dl | 69.7 | 78 | 12 |
| LDL-cholesterol | mg/dl | 95.3 | 100 | 5 |
| glucose | mg/dl | 88.0 | 84 | −5 |
| ferritin | µg/l | 188.0 | 137 | −27 |
| erythrocytes | Mio/µl | 5.0 | 5.08 | 2 |
| haemoglobin | g/dl | 14.3 | 14.6 | 2 |
| hematocrit | l/l | 0.4 | 0.442 | 7 |
| MCV | fL | 84.0 | 87 | 4 |
| MCH | pg | 28.7 | 29 | 1 |
| MCHC | g/dl | 34.3 | 33 | −4 |
| thrombocytes | /nl | 205.0 | 184 | −10 |
| tsh basal | µU/ml | 1.3 | 2.29 | 82 |

The treatment with 2-aminomethanesulfonic acid causes a more than 40% decrease of the total bilirubin value;

an almost 40% decrease in the triglyceride value;

a more than 25% reduction of the ferritin value; and a more than 80% increase in the basal tsh value.

For a person skilled in the art these changes are unexpected and surprising. In particular the decrease of the total bilirubin value despite the patient's UGT1A1*28/*28 genotype appears puzzling as does the highly significant increase of the tsh basal value which is highly relevant for the activity of the thyroid gland and the basal metabolic rate.

EXAMPLE 13

5 mg Olanzapine and 250 mg 2-aminoethane-sulfonic Acid Tablet

| Constituents | mg per tablet | % per tablet |
|---|---|---|
| Olanzapine | 5 | 1.25 |
| Taurine | 250 | 62.50 |
| Microcrystalline cellulose | 25 | 6.25 |
| Mannitol | 10 | 2.50 |
| Povidone | 10 | 2.50 |
| Sorbitol | 98 | 24.50 |
| Magnesium stearate | 2 | 0.50 |
| Total Olanzapine layer | 400 | 100.00 |

EXAMPLE 14

80 mg Fenofibrate and 250 mg 2-aminoethane-sulfonic Acid Tablet

| Constituents | mg per tablet | % per tablet |
|---|---|---|
| Fenofibrate | 80 | 20.00 |
| Taurine | 250 | 62.50 |
| Microcrystalline cellulose | 28 | 7.00 |
| Mannitol | 10 | 2.50 |
| Povidone | 10 | 2.50 |
| Pregelatinized atarch | 20 | 5.00 |
| Magnesium stearate | 2 | 0.50 |
| Total Fenofibrate layer | 400 | 100.00 |

The invention claimed is:

1. A pharmaceutical preparation for oral administration comprising 250-1000 mg 2-aminoethanesulfonic acid and an antihypertensive agent selected from the group consisting of telmisartan, irbesartan, valsartan, olmesartan, and azilsartan or a pharmaceutically acceptable salt thereof in admixture with one or more excipients selected from the group consisting of mannitol, sorbitol, xylitol, saccharose, calcium carbonate, calcium phosphate, lactose, croscarmellose sodium salt, crospovidone, sodium starch glycolate, hydroxypropylcellulose (low substituted), maize starch, polyvinylpyrrolidone, copolymers of vinylpyrrolidone with other vinyl derivatives, hydroxypropyl cellulose, hydroxypropylmethyl cellulose, microcrystalline cellulose or starch, magnesium stearate, sodium stearyl fumarate, talc, hydroxypropylmethylcellulose, carboxymethylcellulose, cellulose acetate phthalate, polyvinylacetate, water, water/ethanol, water/glycerine, water/sorbitol, water/polyethylene glycol, propylene glycol, cetylstearyl alcohol, carboxymethylcellulose or substance containing fat.

2. The preparation according to claim 1, characterized in that the preparation contains 20-200 mg of the angiotensin blocker telmisartan.

3. The preparation according to claim 1, wherein the preparation is effective to lower the bilirubin level of a hypertensive individual having unconjugated hyperbilirubinemia.

4. The preparation according to claim 3, wherein the preparation is effective to lower the bilirubin level of a hypertensive individual with an UGT1A1*28 allele.

5. The preparation according to claim 1 wherein the antihypertensive agent is irbesartan.

6. The preparation according to claim 1 wherein the antihypertensive agent is valsartan.

7. The preparation according to claim 1 wherein the antihypertensive agent is olmesartan.

* * * * *